(12) United States Patent
Cash

(10) Patent No.: US 10,548,814 B2
(45) Date of Patent: Feb. 4, 2020

(54) INTRAORAL FLUID DELIVERY SYSTEM AND METHOD

(71) Applicant: Jeffrey Ward Cash, Richmond, VA (US)

(72) Inventor: Jeffrey Ward Cash, Richmond, VA (US)

( * ) Notice: Subject to any disclaimer, the term of this patent is extended or adjusted under 35 U.S.C. 154(b) by 1097 days.

(21) Appl. No.: 14/613,803

(22) Filed: Feb. 4, 2015

(65) Prior Publication Data

US 2015/0328084 A1    Nov. 19, 2015

Related U.S. Application Data

(60) Provisional application No. 62/000,377, filed on May 19, 2014.

(51) Int. Cl.
| | | |
|---|---|---|
| *A61J 7/00* | (2006.01) | |
| *A61C 19/06* | (2006.01) | |
| *A61C 17/02* | (2006.01) | |
| *A61M 5/142* | (2006.01) | |

(52) U.S. Cl.
CPC ........... *A61J 7/0053* (2013.01); *A61C 19/063* (2013.01); *A61J 7/0015* (2013.01); *A61J 7/0046* (2013.01); *A61J 7/0092* (2013.01); *A61C 17/0211* (2013.01); *A61M 5/14276* (2013.01)

(58) Field of Classification Search
CPC .......... A61M 25/02; A61M 2025/0206; A61M 2025/022; A61J 7/0053; A61J 7/0092; A61C 19/063; A61C 17/0211
See application file for complete search history.

(56) References Cited

U.S. PATENT DOCUMENTS

| | | | | |
|---|---|---|---|---|
| 3,683,907 A | * | 8/1972 | Cotabish | A62B 18/003 128/200.28 |
| 4,665,566 A | * | 5/1987 | Garrow | A61M 16/0666 128/201.22 |
| 5,566,645 A | * | 10/1996 | Cole | A01K 15/02 119/712 |
| 5,984,145 A | * | 11/1999 | McAllister | A45F 3/16 222/175 |
| 6,619,288 B2 | * | 9/2003 | Demers | A61M 16/06 128/205.25 |
| 8,434,493 B1 | * | 5/2013 | McGhie | H04R 1/1066 128/200.24 |

(Continued)

OTHER PUBLICATIONS

Lorin Technologies Corp., 510(k) Submission for Xeros Dry Mouth Pump, Apr. 8, 2011, 7 pages.

*Primary Examiner* — Jenna Zhang
(74) *Attorney, Agent, or Firm* — Troutman Sanders LLP; Christopher J. Forstner; John A. Morrissett

(57) ABSTRACT

A system for intraoral fluid delivery comprises a rate-controlled and/or volume-controlled fluid supply device, a reservoir for holding one or more fluids to be delivered to a patient's oral cavity, a mouthpiece to be worn by a patient at least partially within the patient's oral cavity, and tubing to carry the one or more fluids from the fluid supply device to the mouthpiece. The mouthpiece comprises a fluid inlet adjacent and/or exterior to the patient's oral cavity when the mouthpiece is worn by the patient, a fluid outlet posterior to the fluid inlet, and a fluid channel therebetween.

11 Claims, 7 Drawing Sheets

(56) References Cited

U.S. PATENT DOCUMENTS

| | | | |
|---|---|---|---|
| 2006/0141423 A1* | 6/2006 | Brown | A61C 19/004 433/215 |
| 2006/0278232 A1* | 12/2006 | Nichols | A61M 16/0666 128/206.11 |
| 2008/0171303 A1* | 7/2008 | Roberts | A61J 15/0011 433/167 |
| 2008/0190436 A1* | 8/2008 | Jaffe | A61M 16/0666 128/207.18 |
| 2010/0016908 A1* | 1/2010 | Martin | A61M 16/0006 607/3 |
| 2010/0180900 A1* | 7/2010 | Talsma | A61M 16/0488 128/207.14 |
| 2011/0124948 A1* | 5/2011 | Yokell | A61M 5/1407 600/5 |
| 2011/0270166 A1* | 11/2011 | Martin | A61J 7/0061 604/79 |
| 2013/0025607 A1* | 1/2013 | Altounian | A61C 19/063 128/861 |
| 2013/0118504 A1 | 5/2013 | Hermanson et al. | |

* cited by examiner

INTRAORAL FLUID DELIVERY SYSTEM AND METHOD

CROSS-REFERENCE TO RELATED APPLICATIONS

This application claims priority to U.S. Provisional Application Ser. No. 62/000,377, filed May 19, 2014, the contents of which are incorporated herein by reference in its entirety.

FIELD OF THE INVENTION

The present disclosure relates generally to medical and dental devices, and more particularly to systems and methods for treating symptoms of chronic dry mouth

BACKGROUND

One of the most difficult problems to overcome related to the care of the human oral cavity is the absence of sufficient saliva to protect the hard and soft tissues. This condition, known as xerostomia, has become more prominent in our society with the lengthening of our lifespan and the large number of medications and treatments prescribed to address a variety of human conditions.

Some prominent examples of induced xerostomia include the use of high blood pressure medications, antidepressants, amphetamine and stimulants for A.D.H.D. treatment, as well as radiation therapy to the head and neck region prescribed to eradicate cancer. In addition, other causes of dry mouth can be related to increased age, systemic disorders (such as Sjogren's syndrome and diabetes), and congenital defects.

The absence of natural saliva places an individual at a significant disadvantage with relation to maintenance of oral health. Patients with acute or chronic xerostomia often suffer from pain, opportunistic infections, dental caries and poor fitting dental prosthetics.

Saliva is composed of numerous proteins, minerals, and immunoglobulins, all designed to protect and preserve the teeth and supporting structures as well as facilitate digestion.

Current modalities of treatment for xerostomia include medications prescribed to increase salivary flow (e.g., pilocarpine), frequent consumption of water during the day, and the use of oral lubricants provided through mouthwashes, gums, and oral sprays. With the exception of medication, all of these techniques provide temporary relief for patients, and can only benefit patients while they are awake.

BRIEF SUMMARY

Briefly stated, one aspect of the present disclosure is directed to a system for intraoral fluid delivery comprising a rate-controlled and/or volume-controlled fluid supply device, a reservoir for holding one or more fluids to be delivered to a patient's oral cavity, a mouthpiece to be worn by a patient at least partially within the patient's oral cavity, and tubing to carry the one or more fluids from the fluid supply device to the mouthpiece. The mouthpiece comprises a fluid inlet adjacent and/or exterior to the patient's oral cavity when the mouthpiece is worn by the patient, a fluid outlet posterior to the fluid inlet, and a fluid channel therebetween.

The rate-controlled and/or volume-controlled fluid supply device may comprise a regulated pumping device. The pumping device may have an adjustable flow rate of between 0.1 milliliter per hour and one liter per hour. The pumping device may be programmable to pump a defined volume of fluid over a defined period of time.

The rate-controlled and/or volume-controlled fluid supply device may comprise intravenous micro-tubing, and the reservoir may comprise an intravenous bag or bottle or any other suitable container that may be connected to the IV tubing.

The fluid outlet may be adjacent a posterior end of the mouthpiece. The fluid outlet may be defined in a buccal or lingual side of the mouthpiece.

The fluid outlet may be a first fluid outlet and the fluid channel may be a first fluid channel. The mouthpiece may further comprise a second fluid outlet posterior to the fluid inlet and a second fluid channel between the fluid inlet and the second fluid outlet.

The system may further comprise a magnetic stirrer for agitating the one or more fluids in the reservoir.

In an alternative embodiment of the invention, a system for intraoral fluid delivery comprises a rate-controlled and/or volume-controlled fluid supply device, a reservoir for holding one or more fluids to be delivered to a patient's oral cavity, a head-worn appliance, and tubing to carry the one or more fluids from the fluid supply device to the appliance. The head-worn appliance comprises a support portion for securing the appliance to a patient's head and a fluid delivery portion supported by the support portion. The fluid delivery portion comprises a fluid conduit having an acute bend and a fluid outlet at a distal end of the fluid conduit for placement within a patient's oral cavity when the appliance is secured to the patient's head.

The rate-controlled and/or volume-controlled fluid supply device may comprise a regulated pumping device. The pumping device may have an adjustable flow rate of between 0.1 milliliter per hour and one liter per hour. The pumping device may be programmable to pump a defined volume of fluid over a defined period of time.

The rate-controlled and/or volume-controlled fluid supply device may comprise intravenous micro-tubing, and the reservoir may comprise an intravenous bag or bottle or any other suitable container that may be connected to the IV tubing.

The system may further comprise a magnetic stirrer for agitating the one or more fluids in the reservoir.

In another alternative embodiment of the invention, a system for intraoral fluid delivery comprises a rate-controlled and/or volume-controlled fluid supply device, a reservoir for holding one or more fluids to be delivered to a patient's oral cavity, a fluid delivery device for delivering the one or more fluids into the patient's oral cavity, tubing to carry the one or more fluids from the fluid supply device to the fluid delivery device, and a magnetic stirrer for agitating the one or more fluids in the reservoir.

The rate-controlled and/or volume-controlled fluid supply device may comprise a regulated pumping device. The pumping device may have an adjustable flow rate of between 0.1 milliliter per hour and one liter per hour. The pumping device may be programmable to pump a defined volume of fluid over a defined period of time.

The rate-controlled and/or volume-controlled fluid supply device may comprise intravenous micro-tubing, and the reservoir may comprise an intravenous bag or bottle or any other suitable container that may be connected to the IV tubing.

The fluid delivery device may comprise a mouthpiece to be worn by a patient at least partially within the patient's oral cavity, the mouthpiece comprising a fluid inlet adjacent and/or exterior to the patient's oral cavity when worn by the patient, a fluid outlet posterior to the fluid inlet, and a fluid channel therebetween. The fluid outlet may be adjacent a posterior end of the mouthpiece. The fluid outlet may be defined in a buccal or lingual side of the mouthpiece.

The fluid outlet may be a first fluid outlet and the fluid channel may be a first fluid channel. The mouthpiece may further comprise a second fluid outlet posterior to the fluid inlet and a second fluid channel between the fluid inlet and the second fluid outlet.

The fluid delivery device may comprise a head-worn appliance, the head-worn appliance comprising a support portion for securing the appliance to a patient's head and a fluid delivery portion supported by the support portion. The fluid delivery portion may comprise a fluid conduit having an acute bend and a fluid outlet at a distal end of the fluid conduit for placement within a patient's oral cavity when the appliance may be secured to the patient's head.

In another alternative embodiment of the invention, a mouthpiece for delivering fluid into a patient's oral cavity comprises a body to be worn by a patient at least partially within the patient's oral cavity, a fluid inlet defined in an anterior portion of the body and adjacent and/or exterior to the patient's oral cavity when the mouthpiece is worn by the patient, a fluid outlet defined in the body posteriorly to the fluid inlet, and a fluid channel defined in the body fluidly connecting the fluid inlet to the fluid outlet.

The fluid outlet may be adjacent a posterior end of the mouthpiece. The fluid outlet may be defined in a buccal or lingual side of the mouthpiece.

The fluid outlet may be a first fluid outlet and the fluid channel may be a first fluid channel. The mouthpiece may further comprise a second fluid outlet defined in the body posteriorly to the fluid inlet and a second fluid channel defined in the body fluidly connecting the fluid inlet and the second fluid outlet.

In another alternative embodiment of the invention, a head-worn appliance for delivering fluid into a patient's oral cavity comprises a support portion for securing the appliance to a patient's head, and a fluid delivery portion supported by the support portion. The fluid delivery portion comprises a fluid conduit having an acute bend and a fluid outlet at a distal end of the fluid conduit for placement within a patient's oral cavity when the appliance is secured to the patient's head.

In another alternative embodiment of the invention, a method of delivering one or more fluids into a patient's oral cavity comprises pumping, using a rate-controlled and/or volume-controlled fluid supply device, the one or more fluids from a reservoir to a mouthpiece to be worn by a patient at least partially within the patient's oral cavity. The mouthpiece comprises a fluid inlet adjacent and/or exterior to the patient's oral cavity when worn by the patient, a fluid outlet posterior to the fluid inlet, and a fluid channel therebetween.

The rate-controlled and/or volume-controlled fluid supply device may comprise a regulated pumping device. The pumping device may have an adjustable flow rate of between 0.1 milliliter per hour and one liter per hour. The pumping device may be programmable to pump a defined volume of fluid over a defined period of time.

The rate-controlled and/or volume-controlled fluid supply device may comprise intravenous micro-tubing, and the reservoir may comprise an intravenous bag or bottle or any other suitable container that may be connected to the IV tubing.

The pumping device may have an adjustable flow rate of between 0.1 milliliter per hour and one liter per hour.

The pumping device may be programmable to pump a defined volume of fluid over a defined period of time.

The fluid outlet may be adjacent a posterior end of the mouthpiece. The fluid outlet may be defined in a buccal or lingual side of the mouthpiece.

The fluid outlet may be a first fluid outlet and the fluid channel may be a first fluid channel. The mouthpiece may further comprise a second fluid outlet posterior to the fluid inlet and a second fluid channel between the fluid inlet and the second fluid outlet.

The method may further comprise stirring, using a magnetic stirrer, the one or more fluids in the reservoir.

BRIEF DESCRIPTION OF THE SEVERAL VIEWS OF THE DRAWING(S)

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings.

DETAILED DESCRIPTION

Figure 1:
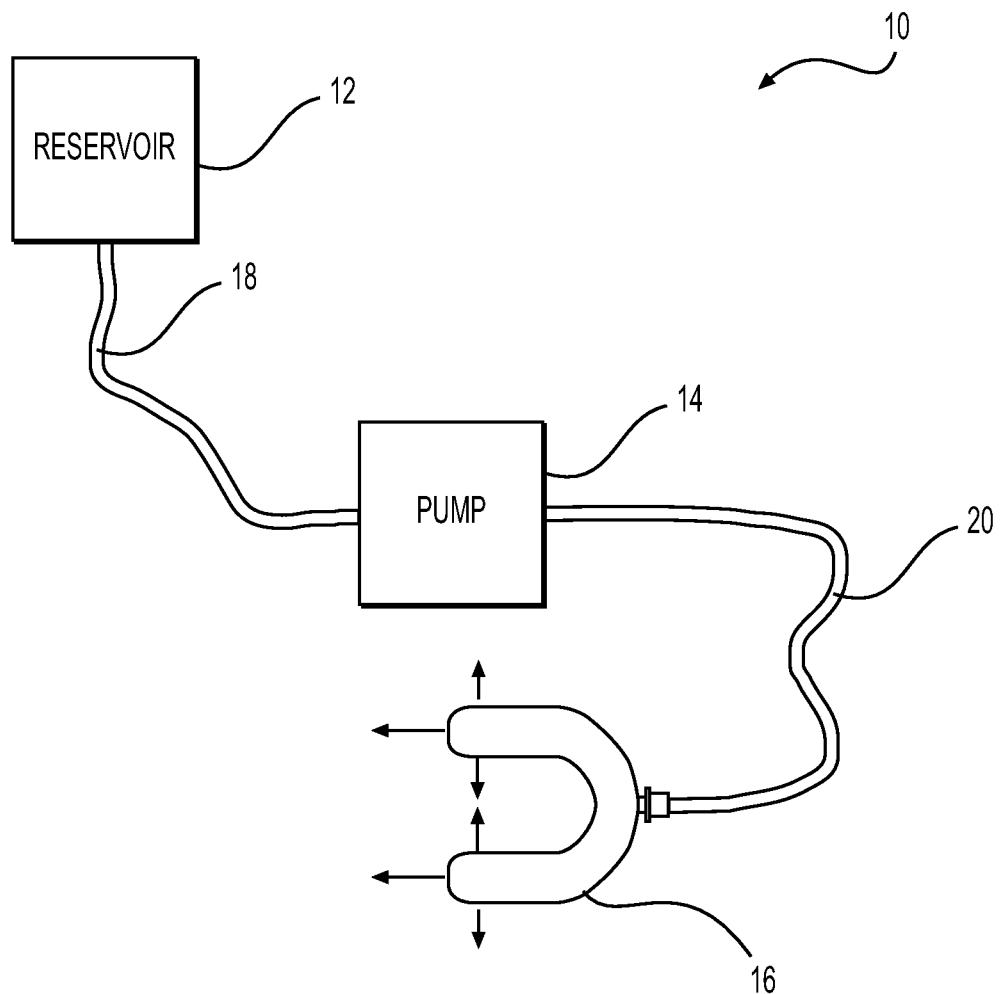
FIG. 1 illustrates a schematic block diagram of a system of intraoral fluid delivery, in accordance with embodiments of the invention.

Certain terminology is used in the following description for convenience only and is not limiting. The words "lower," "bottom," "upper," and "top" designate directions in the drawings to which reference is made. The words "inwardly," "outwardly," "upwardly" and "downwardly" refer to directions toward and away from, respectively, the geometric center of the device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

Embodiments of the invention enable a dental or medical practitioner to treat individuals suffering with xerostomia using a system and method by which missing fluids can predictably be replaced at a controlled volume and rate. These replacement fluids can be basic salivary substitutes for the relief of dry mouth or could comprise medicinal agents to treat various illnesses. Importantly, embodiments of the invention enable treatment of xerostomia during the sleeping hours when patients cannot supplement themselves.

Referring to the drawings in detail, wherein like numerals indicate like elements throughout, FIG. 1 illustrates a schematic block diagram (not to scale) of a system of intraoral fluid delivery, in accordance with embodiments of the invention. The system 10 for intraoral fluid delivery comprises a regulated pumping device 14, a reservoir 12 for holding one or more fluids to be delivered to a patient's oral cavity, a mouthpiece 16 to be worn by a patient at least partially within the patient's oral cavity, tubing 18 to carry the one or more fluids from the reservoir 12 to the pumping device 14, and tubing 20 to carry the one or more fluids from the pumping device 14 to the mouthpiece 16 (or alternative fluid delivery device, as described further below).

Reservoir 12 is designed to hold the fluid or fluids that will be delivered to the oral cavity. Reservoir 12 can be a solid container (e.g., glass or rigid plastic) or a collapsible intravenous (I.V.) fluid-type bag. This container will be such that liquids can be stored inside and protected from the surrounding environment, to help ensure that whatever is administered into the patient's mouth is not contaminated with environmental agents. Reservoir 12 may be refillable by the patient when necessary, or reservoir 12 can be pre-filled, single-use, and disposable (like a collapsible sterile I.V. bag). The type of container to be used will typically be determined by the health care prescriber and, if reusable, should be easily cleansable.

In an alternative embodiment of the invention, multiple reservoirs may be used such that one or more different fluids are delivery from each of the different reservoirs (commonly referred to as "piggybacks" or "secondary" fluids in the medical field).

The tubing 18 from the reservoir 12 to the pumping device 14 and the tubing 20 from the pumping device 14 to the mouthpiece 16 (or other device) may comprise two separate tubing sections (from the reservoir to the pumping device and from the pumping device to the mouthpiece) or (more likely) may comprise a single, unitary tubing section (from the reservoir through the pumping device to the mouthpiece). Tubing 18, 20 may comprise standard I.V. tubing or any other suitable tubing. Tubing 20 may connect to a port (described further below) in the mouthpiece through a connection like those that attach I.V. lines and syringes (commonly known as a Luer Lock) or any other suitable method. The tubing can be of any desired length to fit a patient's needs since the length of the tubing does not affect the function of the invention. The tubing should typically be disposable to prevent the growth of bacteria or cross contamination should the system be shared between patients.

Pumping device 14 propels the one or more fluids from the reservoir 12 to the mouthpiece 16 (or other similar device) (via tubes 18 and 20) and out of the mouthpiece into the patient's oral cavity (assuming that the mouthpiece is in place in the patient's oral cavity). The pumping device 14 may be the same type of pump that is used to deliver intravenous fluids and medications (commonly referred to as infusion pumps or PCA (patient controlled analgesia) pumps. The pumping device 14 must be able to regulate the flow rate of the fluid(s) to the mouthpiece 16 so that a desired and specified amount of liquid can be delivered at a desired and specified flow rate, the amount of liquid and/or the flow rate being specific to a patient's needs. The pumping device 14 should have an adjustable flow rate capable of delivering as little as 0.1 milliliter per hour (ml/hr) to as much as 1 liter per hour (L/hr) of fluid. In addition, the pumping device 14 should have a setting to pump a defined total volume to be infused (V.T.B.I.) over a defined amount of time. These settings are important because if the patient uses the system while sleeping, the flow rate must be properly adjusted to prevent fluid aspiration and choking. Also, if medications are to be administered in the fluids, the health care provider must be assured that overdosing is prevented and that the V.T.B.I. is not exceeded. The pumping device may have time-based adjustable flow rates, such that different flow rates are used at different times of day. Such time-based flow rates are typically based on normal salivary flow at specific times of day. The pumping device may be corded and powered by plugging in to an AC wall outlet, and/or the pumping device may be cordless and powered by an internal or external battery(ies) or battery pack for portability. A carrying case (e.g., "fanny pack") may be used to transport the components of the system. A wireless remote control may be used to control the pumping device.

In alternative embodiments of the invention, the pumping device may be omitted and a gravity-fed device may provide fluid to the mouthpiece. Such a gravity-fed device may comprise IV tubing, typically micro-drip tubing (60 drops equals 1 milliliter), in which case the IV bag (or any other suitable container that may be connected to the IV tubing) would comprise the reservoir.

A mouthpiece of embodiments of the invention may comprise any suitable structure that includes a body portion to be worn by a patient at least partially within the patient's oral cavity, a fluid inlet defined in an anterior portion of the body, one or more fluid outlets defined in the body posteriorly to the fluid inlet, and one or more fluid channels defined in the body that fluidly connect the fluid inlet to the fluid outlet(s), thereby enabling the pumped fluid(s) to be directed to desired location(s) within the patient's oral cavity. The shape and size of the mouthpiece may vary greatly depending on a number of different factors, including but not limited to the size and shape of the patient's oral cavity, whether the mouthpiece is to be worn when the patient is awake or asleep, the amount and/or flow of fluid to be delivered, the location(s) within the patient's oral cavity to which the fluid is to be delivered, the patient's comfort level and tolerance of keeping such an object in their mouth, the existence and condition of the patient's teeth, the presence of any dental appliances (e.g., full or partial dentures, bridges, etc.) and the material(s) of which the mouthpiece is to be constructed.

Mouthpieces of embodiments of the invention generally fall into one of two categories: (1) mouthpieces that at least partially cover some or all of the teeth (upper and/or lower), such as is illustrated in FIGS. 3-6; and (2) mouthpieces that sit between the teeth (upper and/or lower) and the cheek and/or lips, such as is illustrated in FIGS. 7-11.

A mouthpiece of embodiments of the invention may be custom molded to the patient's oral cavity and teeth, or may have a standard, fixed shape/contour. For example, the mouthpiece can be prefabricated out of thermoplastic then warmed in hot water and fitted to an individual's mouth (as is customarily seen in over the counter sports guards), or the mouthpiece can be fabricated by a licensed dentist and/or dental laboratory using custom impressions. Patients with extensive dental fixed prosthetics (e.g., crowns and implants) or who are missing teeth and wear removable prosthetics should generally have a dental professional fabricate the mouthpiece.

The fluid inlet is typically adjacent and/or exterior to the patient's oral cavity when the mouthpiece is worn by the patient. That is, the fluid inlet is typically close to the patient's lips, and may be inside or outside of the patient's lips when the mouthpiece is worn. The fluid inlet may be centered at the anterior (front) portion of the mouthpiece, or may be offset to the left or right side. A mouthpiece of embodiments of the invention could theoretically have more than one inlet, but that would not typically be necessary and would add additional cost and complexity to the system.

A mouthpiece of embodiments of the invention may have any desired number of fluid outlets, and the fluid outlets may have any desired location(s). As indicated in FIG. 1 by the arrows adjacent the mouthpiece 16, the mouthpiece may have fluid outlets that direct the fluid(s) toward the tongue (i.e., out the lingual side(s) of the mouthpiece), toward the cheek (i.e., out the buccal side(s) of the mouthpiece) and/or out the posterior end(s) of the mouthpiece. The fluid outlet(s) may face the cheek, one or more specific teeth, specific locations on the attached gingiva or the mucosa, etc. The locations of the fluid outlet(s) may be selected by the practitioner to suit different needs, such as dry mouth, wound healing, infection control, periodontal therapy, etc.

Figure 8:
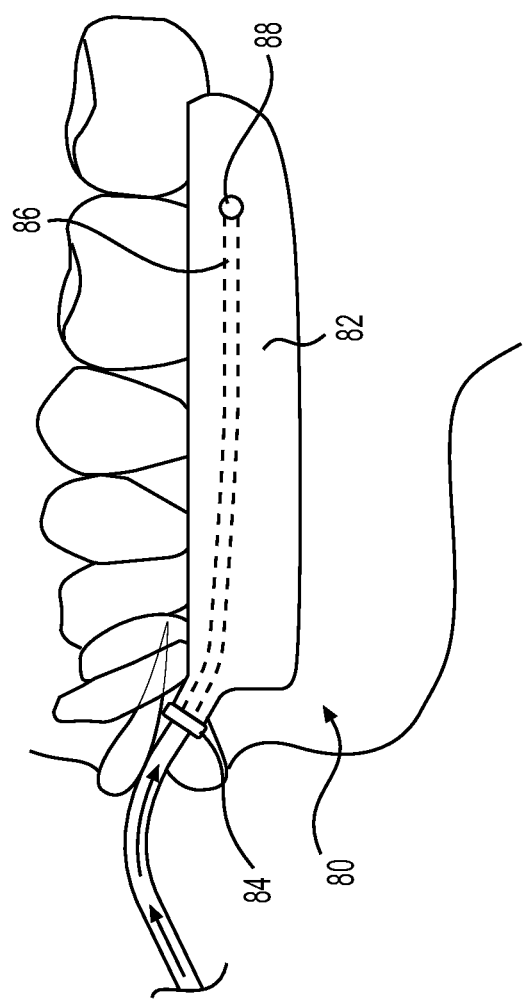
Figure 9:
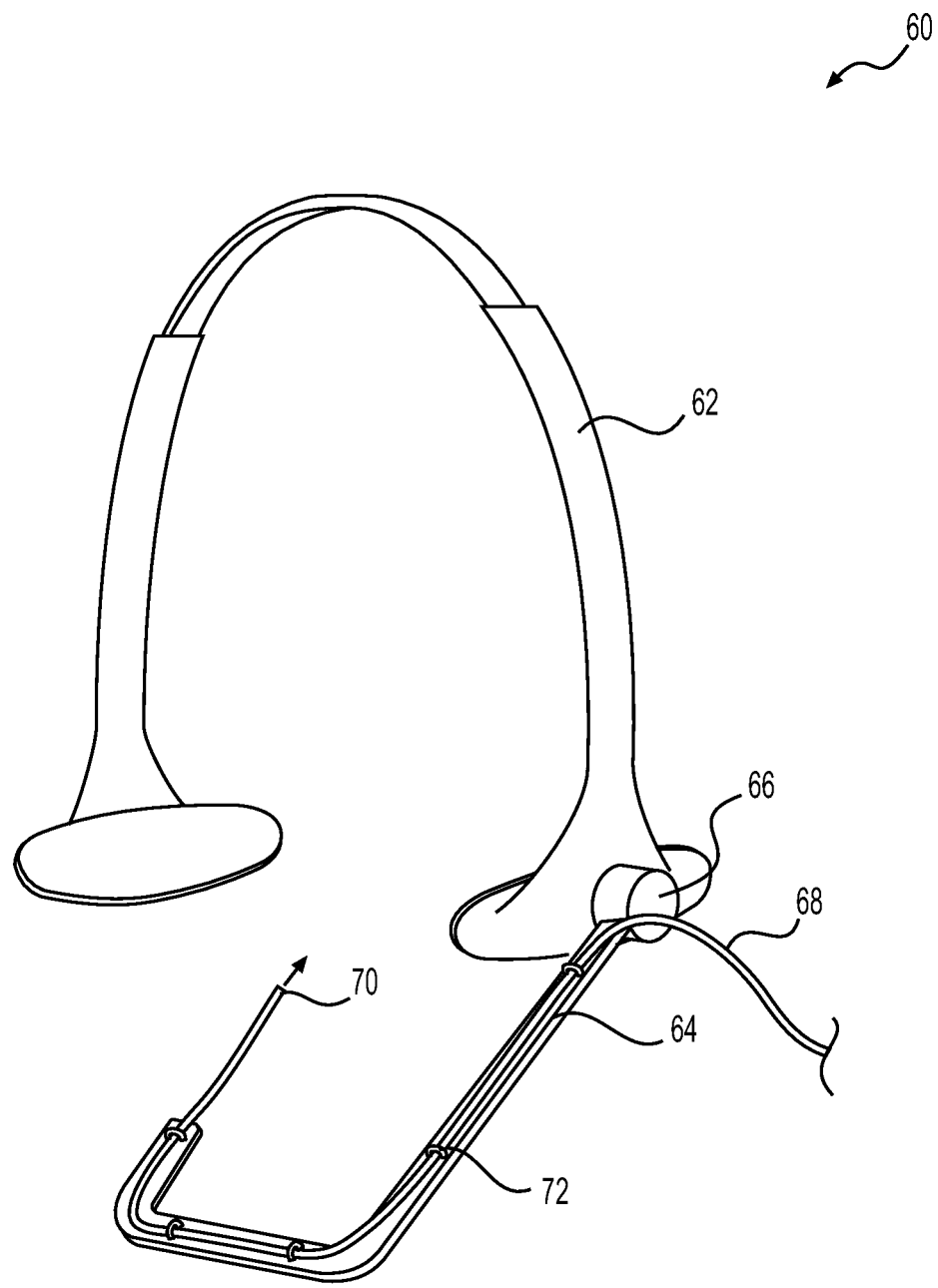
FIG. 9 illustrates an alternative fluid delivery device of the system of FIG. 1.
Figure 10:
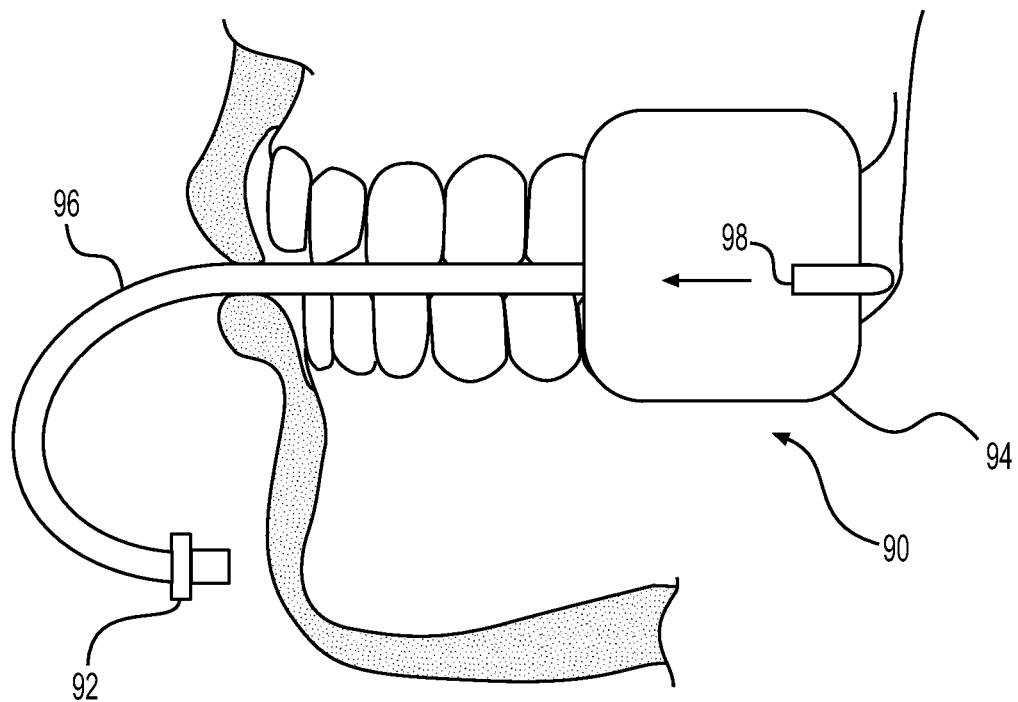
FIGS. 10 and 11 are side and top views, respectively, of an alternate type of mouthpiece of the system of FIG. 1.
Figure 11:
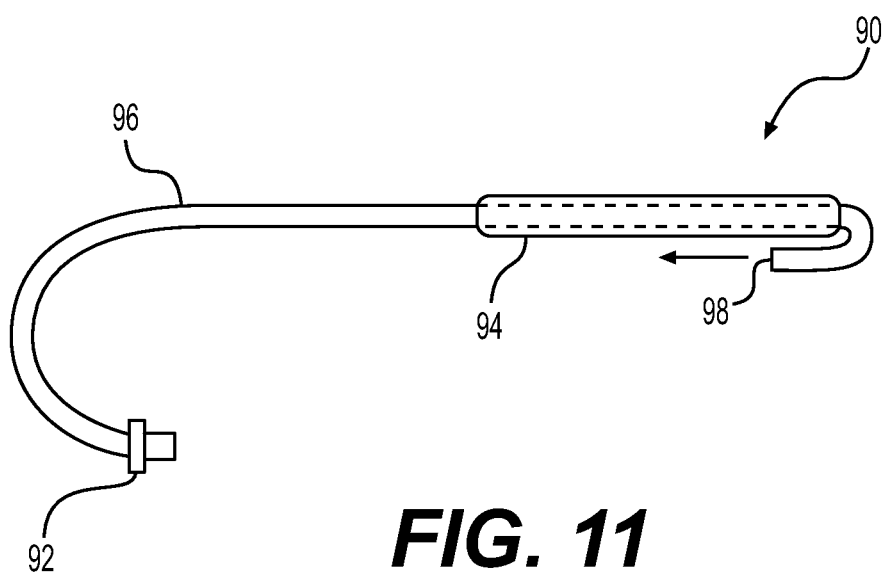

The mouthpiece may be single level and positionable adjacent to (or attachable to) the top teeth or the bottom teeth. Alternatively, the mouthpiece may be double level and positionable adjacent to (or attachable to) both the top teeth and the bottom teeth. Such a double level mouthpiece may have fluid outlets on one or both levels. The mouthpiece may be single sided such that it is positionable adjacent to (or attachable to) the teeth on one side of the oral cavity or the other. Alternatively, the mouthpiece may be double sided such that it is positionable adjacent to (or attachable to) the teeth on both sides of the oral cavity at the same time. Such a double-sided mouthpiece may have fluid outlets on one or both sides. As an example, mouthpiece 16 described below and illustrated in FIGS. 3-6 is both double level and double sided. In contrast, mouthpiece 80 described below and illustrated in FIGS. 8-9 is single level and double sided (mouthpiece 80 is perhaps a more likely commercial embodiment of the invention). In further contrast, mouthpiece 90 described below and illustrated in FIGS. 10-11 is single sided and may be sized such that it sits adjacent only the lower teeth, only the upper teeth, or both the upper and lower teeth (as illustrated).

A mouthpiece of embodiments of the invention may attach to and be supported by the patient's teeth. Such attachment may be frictional, similar to an orthodontic retainer or dental bite guard (such frictional retention will typically require that the mouthpiece be molded to the patient's teeth). Alternatively, such attachment may be via mechanical fasteners, such as ball clasps that engage the interproximal embrasure between the teeth, similar to partial dentures. Supporting the mouthpiece by the teeth may be desirable for patients who need to guard against tissue trauma (e.g., patients receiving radiation treatment).

A mouthpiece of embodiments of the invention may be constructed of any suitable material or combination of materials, including but not limited to soft atraumatic material like dental grade silicone or polyvinyl siloxane, more rigid material like dental acrylic, or combinations of soft and rigid materials.

A mouthpiece of embodiments of the invention may comprise an optional additional material or materials that is/are attached to or incorporated in the mouthpiece, to provide additional functionality that may be necessary to treat specific individual patients. For example, absorptive material (e.g., sponge) may be attached to the mouthpiece at or near the fluid outlet(s) to help hold fluid in certain areas longer to increase exposure.

Figure 2:
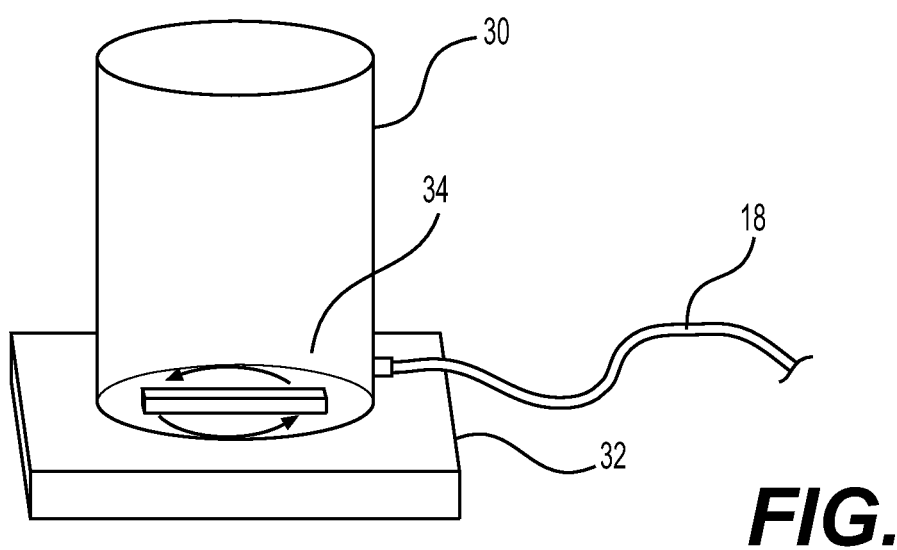
FIG. 2 illustrates an alternative reservoir of the system of FIG. 1
Figure 3:
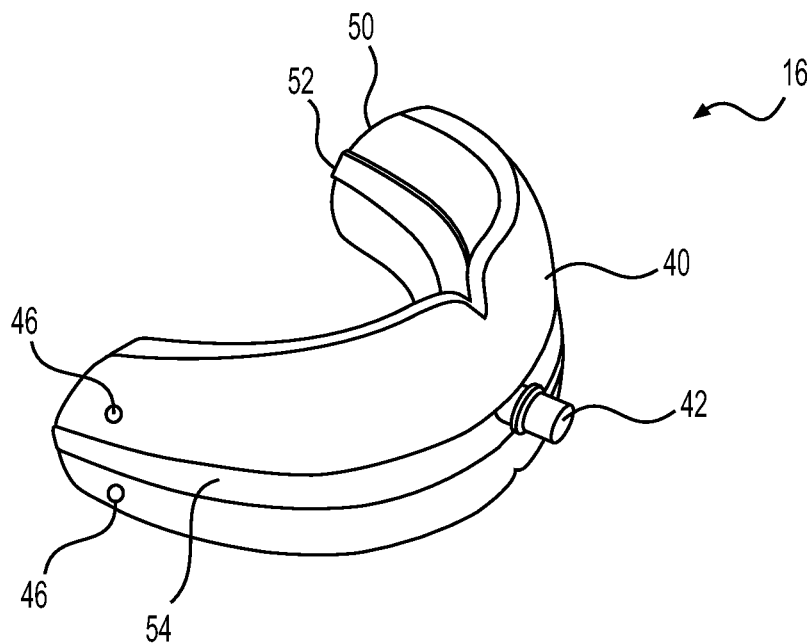
FIGS. 3-6 are perspective, front, side and top views, respectively, of one type of mouthpiece of the system of FIG. 1.

Referring now to FIG. 2, an alternative reservoir is illustrated that uses a magnetic stirrer to mix the contents of the reservoir. Reservoir 30 of FIG. 2 comprises a rigid container (typically but not necessarily cylindrical) sitting on a magnetic stirrer plate 32 and having a magnetic stir bar 34 sitting inside the container. The magnetic stirrer plate 32 produces a rotating magnetic field to cause the stir bar 34 to spin very quickly, thus stirring the contents of the container. Stirring the content of the reservoir 30 may be desirable when a medication has been added to the fluid(s) or when otherwise the reservoir contains a suspension that needs to be agitated (constantly or periodically) to maintain the proper dispersion. Tubing 18 carries the fluid(s) from the reservoir 30 to the pumping device (not illustrated) as described above.

Referring now to FIGS. 3-6, one type of mouthpiece is illustrated that may be used with the system of FIG. 1. Mouthpiece 16 of FIGS. 3-6 is a double level, double sided mouthpiece. Mouthpiece 16 comprises a body 40 with an outer wall 50, an inner wall 52, and a horizontal shelf 54, such that a pocket for the top teeth is formed above the shelf by the two walls and the shelf, and a pocket for the bottom teeth is formed below the shelf by the two walls and the shelf. In this regard, mouthpiece 16 is similar in structure to a boxing mouth guard.

Mouthpiece 16 is a unitary structure, such that movement of the bottom teeth independent of the top teeth is impossible when mouthpiece 16 is in place. Such restriction of independent movement of the bottom teeth is generally not desirable, and therefore, such a unitary double level structure may not be desirable. More typically, a single level mouthpiece (either top or bottom) would be preferable. Such a single level mouthpiece would typically resemble either the top half or the bottom half of mouthpiece 16, although many different structures may be possible. If a double level mouthpiece is desired, two independent single level mouthpieces (top and bottom) may be used.

Figure 4:
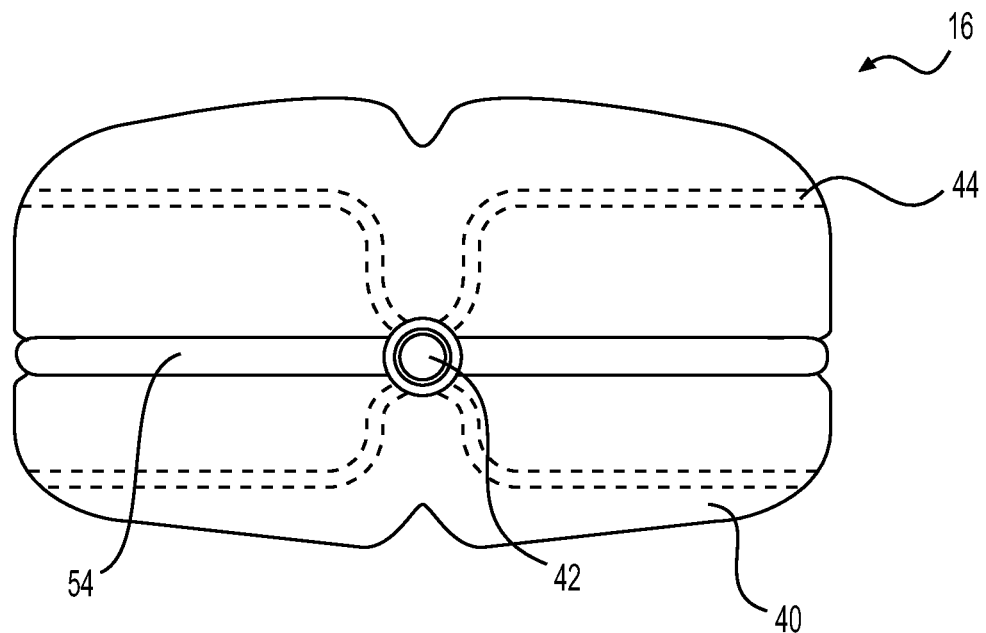
Figure 5:
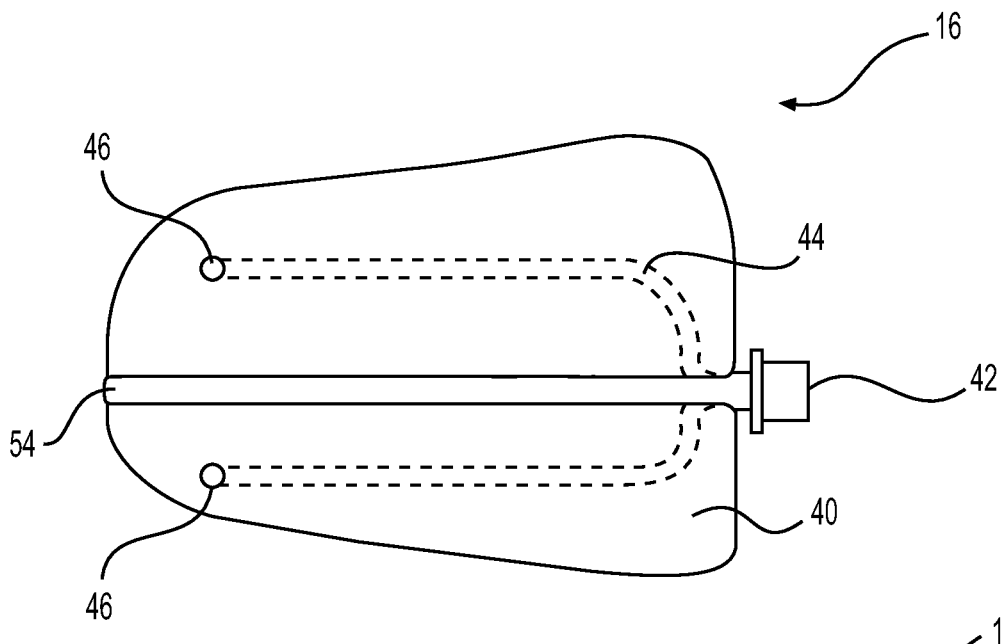
Figure 6:
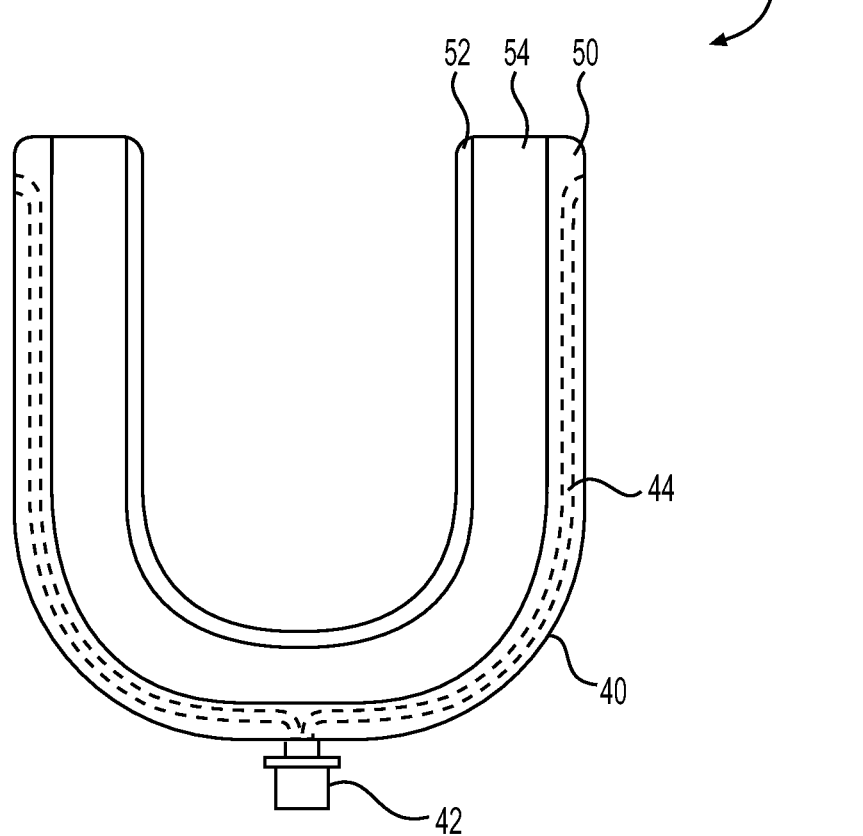

In mouthpiece 16, four fluid channels 44 are defined in the outer wall, as illustrated by the dashed lines in FIGS. 4-6. Each fluid channel leads from fluid inlet 42 to a respective one of four fluid outlets 46 defined in the outer walls adjacent the posterior end of the mouthpiece. In mouthpiece 16, there is an upper right channel and outlet, an upper left channel and outlet, a lower right channel and outlet, and a lower left channel and outlet. As discussed above, alternative embodiments of the invention could use more or fewer channels and outlets.

In use, the mouthpiece 16 is inserted into the patient's mouth such that the patient's top teeth are in the top pocket and the patient's bottom teeth are in the bottom pocket. The tubing (such as tubing 20) is attached to the fluid inlet 42 and the pumping device (such as pumping device 14) is activated. The pumped fluid(s) will exit the mouthpiece from outlets 46 into the patient's oral cavity at the four desired locations.

Figure 7:
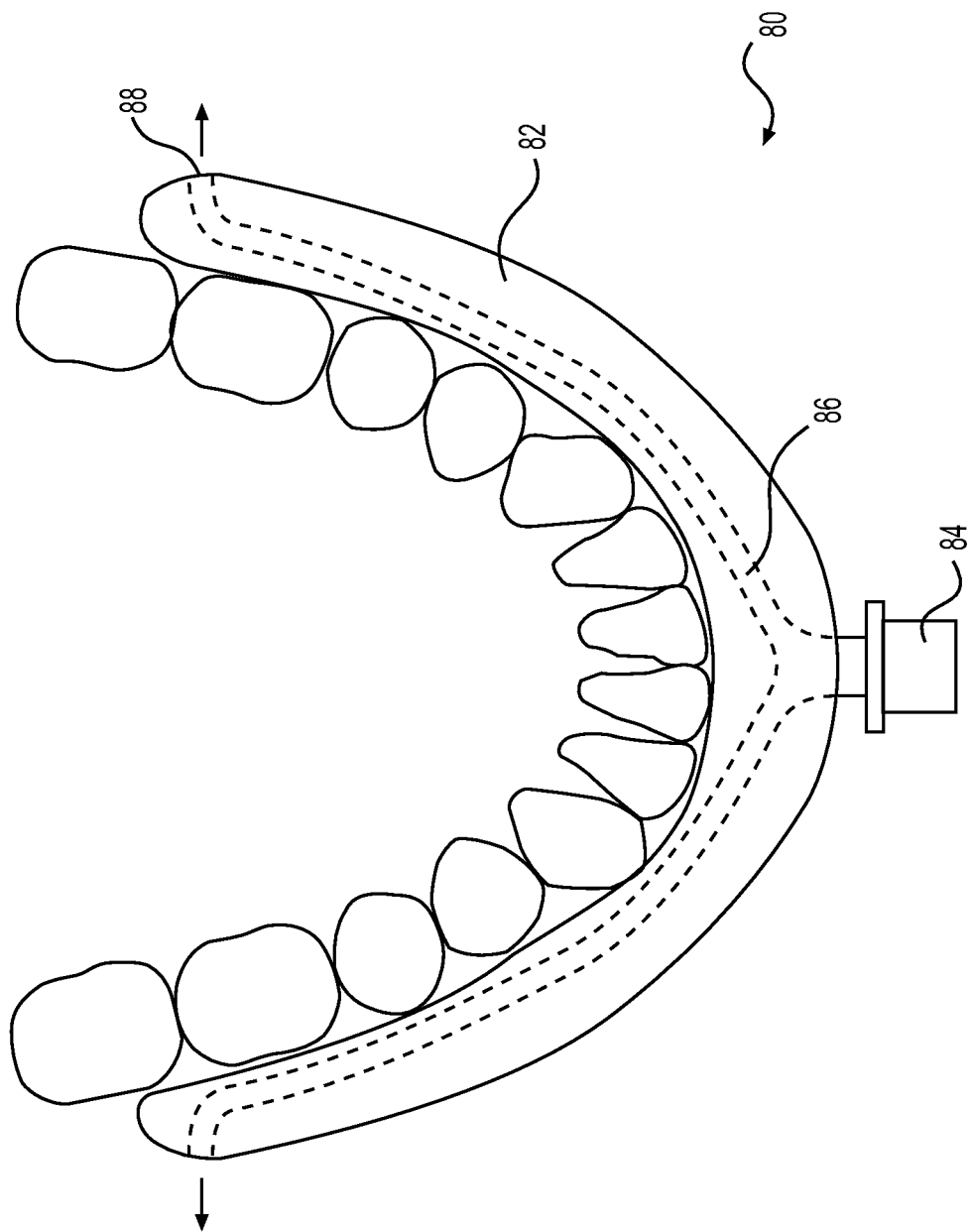
FIGS. 7 and 8 are top and side views, respectively, of an alternate type of mouthpiece of the system of FIG. 1.

Referring now to FIGS. 7 and 8 in which top and side views, respectively, of an alternate type of mouthpiece are illustrated. Mouthpiece 80 of FIGS. 7 and 8 is a single level, double-sided mouthpiece. FIGS. 7 and 8 illustrate mouthpiece 80 in position around a patient's lower teeth. Mouthpiece 80 comprises a generally U-shaped body 82. Body 82 may be flexible to enable the patient to adjust its overall shape to generally conform to the overall arc of the patient's teeth (as illustrated), or body 82 may be moldable to more closely conform to the patient's individual teeth. Two fluid channels 86 are defined in the body 82, as illustrated by the dashed lines in FIGS. 7 and 8. Each fluid channel leads from fluid inlet 84 to a respective one of two fluid outlets 88 defined in the body adjacent the posterior ends of the mouthpiece. In mouthpiece 80, there is a right channel and a left channel. As discussed above, alternative embodiments of the invention could use more or fewer channels and outlets.

In use, the mouthpiece 80 is inserted into the patient's mouth between the patient's teeth (top or bottom) and cheek/lip. Tubing (such as tubing 20) is attached to the fluid inlet 84 and the pumping device (such as pumping device 14) is activated. The pumped fluid(s) will exit the mouthpiece from outlets 88 into the patient's oral cavity at the two desired locations.

When the mouthpiece 80 of FIGS. 7 and 8 is worn by a patient, the two sides of the body 82 (and therefore the two fluid channels 86) follow the "buccal fold/corridor" to end approximately where the Parotid gland secretes into the mouth (known as Stensens' duct). The openings 88 of the channels are advantageously directed towards the cheek to allow for the deposited fluid/suspension to exit and "trickle" down the buccal mucosa. This should help prevent dripping of fluids into the pharynx and stimulation of the glossopharyngeal nerve, thereby reducing the likelihood of coughing, gagging and aspiration.

Referring now to FIG. 9, an alternative fluid delivery device is illustrated for use with embodiments of the invention. Fluid delivery device 60 of FIG. 9 is an alternative to using a mouthpiece (e.g., mouthpiece 16) with an intraoral fluid delivery system of embodiments of the invention. Fluid delivery device 60 may be termed a head-worn appliance. Such a head-worn appliance may be desirable for use when the patient is awake and moving about, as much less structure is be placed within the patient's oral cavity with use of such a head-worn appliance, thereby causing less speech impediment than the mouthpiece might cause.

Fluid delivery device 60 of FIG. 9 comprises a support portion 62 for securing the appliance to a patient's head, and a fluid delivery portion supported by the support portion. The fluid delivery portion comprises a fluid conduit 68 (e.g., tubing) held in a desired position by a boom 64 (or any other suitable mechanism for holding the fluid conduit in the desired position, or no mechanism as described below). The fluid conduit 68 is affixed to the boom 64 via clips 72 or any other suitable mechanism. Boom 64 is affixed to the support portion 62 at attachment point 66. Attachment point 66 may be a pivot point such that the boom 64 can pivot up and down to attain a desired position. Attachment point 66 may have a locking mechanism to lock the boom 64 in the desired position once attained.

Support portion 62 resembles the support portion of conventional audio headphones, in that the support portion 62 is generally upside-down U-shaped, such that the support portion sits comfortably on a patient's head. The support portion may be adjustable, similar to conventional audio headphones, to fit different size heads.

The fluid conduit 68 may be separate from and connect to the tubing from the pumping device (in which case, the proximal end of the fluid conduit would have a Luer Lock or similar connector (not illustrated)), or the fluid conduit 68 may simply be the distal portion of the tubing from the pumping device. If the fluid conduit 68 is separate from and connects to the tubing from the pumping device, the fluid conduit 68 may be the same type of tubing (e.g., I.V. tubing) or may be a different type of tubing. For example, fluid conduit 68 may be constructed out of (or housed within) a malleable, shape-retaining material to enable the patient to form the fluid conduit into the desired shape/position, without requiring a boom 64 or other similar mechanism to hold the fluid conduit in the desired shape/position.

The fluid conduit 68 has an acute bend (either because the patient has formed the fluid conduit to have such a bend, or because the boom 64 is imparting such a bend), as seen in FIG. 9. This acute bend enables the fluid conduit 68, in use, to run alongside the exterior of the patient's face/cheek, and then turn approximately 180 degrees to enable the distal end 70 of the fluid conduit (which is the fluid outlet) to be placed into the patient's oral cavity when the appliance is secured to the patient's head.

In use, the headset 60 is placed on the patient's mouth head, in a manner similar to audio headphones. The position of the boom 64 is adjusted so that the distal end of the boom is near the patient's mouth and the distal end 70 of the fluid conduit is placed into the patient's oral cavity, such that the fluid conduit runs along the "buccal fold/corridor" and ends approximately where the Parotid gland secretes into the mouth. The fluid conduit is attached to the tubing from the pumping device (if separate) and the pumping device (such as pumping device 14) is activated. The pumped fluid(s) will exit the distal end 70 of the fluid conduit into the patient's oral cavity at the desired location. The head worn appliance of FIG. 9 is one-sided, in that there is only one fluid conduit to deliver fluid into one side of the patient's oral cavity. However, alternative embodiments of the invention may be two-sided and have fluid conduits that deliver fluid into both sides of the patient's oral cavity.

In alternative embodiments of the invention, a head worn fluid delivery device may be supported only on the patient's ear, rather than by the top of the patient's head.

While a headset is only illustrated in use with a fluid conduit (e.g., tubing) held in a desired position by a boom (or any other suitable mechanism), as shown in FIG. 9, a headset may be used with any of the mouthpieces to retain the tubing in a desired position.

Referring now to FIGS. 10 and 11 in which side and top views, respectively, of an alternate type of mouthpiece are illustrated. Mouthpiece 90 of FIGS. 10 and 11 is single sided (although two could be used in tandem on both sides of a patient's mouth) and may be sized such that it sits adjacent only the lower teeth, only the upper teeth, or both the upper and lower teeth (as illustrated). FIG. 10 illustrates mouthpiece 90 in position between a patient's teeth and cheek. Mouthpiece 90 comprises a generally square body 94 with rounded corners for comfort (although the body may be any suitable shape, such as oval, round, or rectangular) and a fairly rigid tube 96 that passes through a channel formed within body 94. The proximal end of the tube has a fluid inlet 92, and the distal end of the tube has a fluid outlet 98. The tube 96 is rigid enough to generally retain its shape, but flexible enough to be comfortable within the patient's mouth. Body 94 is constructed of a flexible material that will be comfortable within the patient's mouth but sturdy enough to retain the tube, such as dental grade silicone or polyvinyl siloxane. The tube 96 may be slidable within the body 94, which would enable adjustment of the body and tube within the patient's mouth. The tube 96 may have a 180 degree distal bend and a 180 degree proximal bend, as illustrated. Alternatively, one or both bends could be omitted, or one or both bends could be less than 180 degrees. The distal bend in the tube 96 helps prevent the tube from coming out of the body 94 and helps deliver the fluid into the buccal fold, while the proximal bend in the tube 96 helps prevent the tube from coming out of the body 94 and helps position the proximal end of the tube adjacent the exterior of the patient's cheek. In an alternative embodiment (not illustrated), the distal end of the tube may be even with the distal edge of the body, such that the distal end of the tube does not project out of the body. In such an arrangement in which one or both of the bends are omitted or in which the distal end of the tube does not project out of the body, the tube would typically need to be affixed within the body to prevent the tube from coming out of the body. The body 94 may be offered in one generic size, or multiple different sizes (e.g., adult/pediatric or large/medium/small). Advantageously, the body 94 would typically not need to be molded or custom fit.

In use, the mouthpiece 90 is inserted into the patient's mouth between the patient's teeth (top or bottom or both) and cheek/lip. Tubing (such as tubing 20) is attached to the fluid inlet 92 and the pumping device (such as pumping device 14) is activated. The pumped fluid(s) will exit the mouthpiece from outlet 98 into the patient's oral cavity at the desired location.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

That which is claimed:

1. A system for intraoral fluid delivery comprising:
   a rate-controlled and/or volume-controlled fluid supply device comprising a regulated pumping device programmable to pump a defined volume of fluid over a defined period of time;
   a reservoir for holding one or more fluids to be delivered to a patient's oral cavity;
   a head-worn appliance comprising a fluid conduit and a fluid outlet at a distal end of the fluid conduit adapted for placement within the patient's oral cavity when the appliance is secured to the patient's head; and
   tubing to carry the one or more fluids from the reservoir via the fluid supply device to the appliance, wherein the pumping device is programmable to have different flow rates based on normal salivary flow at specific times of day.

2. The system of claim 1, wherein the pumping device has an adjustable flow rate of between 0.1 milliliter per hour and one liter per hour.

3. The system of claim 1, wherein the rate-controlled and/or volume-controlled fluid supply device comprises intravenous micro-tubing, and wherein the reservoir comprises an intravenous bag or bottle.

4. The system of claim 1, further comprising:
   a magnetic stirrer for agitating the one or more fluids in the reservoir.

5. The system of claim 1, wherein the fluid conduit comprises a malleable, shape-retaining fluid conduit.

6. The system of claim 1, wherein the head-worn appliance further comprises a support portion; and wherein the support portion of the head-worn appliance is adapted to be securable to the patient's ear.

7. The system of claim 1, wherein the head-worn appliance having a fluid delivery portion comprising the fluid conduit and the fluid outlet; and wherein the fluid delivery portion further comprises a mouthpiece through which the fluid conduit passes, the mouthpiece adapted to be positioned in the patient's mouth adjacent one of the patient's checks to retain the fluid conduit in a desired position in the patient's mouth.

8. The system of claim 7, wherein the mouthpiece is generally planar.

9. The system of claim 7, wherein the mouthpiece comprises a flexible material.

10. The system of claim 7, wherein the mouthpiece is constructed of dental grade silicone or polyvinyl siloxane.

11. A system for intraoral fluid delivery comprising:
    a rate-controlled and/or volume-controlled fluid supply device comprising a regulated pumping device programmable to pump a defined volume of fluid over a defined period of time;
    a reservoir for holding one or more fluids to be delivered to a patient's oral cavity;
    a head-worn appliance comprising a fluid conduit and a fluid outlet at a distal end of the fluid conduit adapted for placement within the patient's oral cavity when the appliance is secured to the patient's head; and
    tubing to carry the one or more fluids from the reservoir via the fluid supply device to the appliance, wherein the pumping device is programmable to have time-based adjustable flow rates, such that the pumping device can pump at different flow rates at different times of day.

* * * * *